United States Patent [19]

Sheets

[11] Patent Number: 4,706,666
[45] Date of Patent: Nov. 17, 1987

[54] POSITIONING IMPLEMENT FOR INTRAOCULAR LENS

[76] Inventor: John H. Sheets, Rte. 5, Box 4801, Odessa, Tex. 79764

[21] Appl. No.: 21,318

[22] Filed: Mar. 3, 1987

[51] Int. Cl.$^4$ .......................... A61B 17/00; A61F 2/16
[52] U.S. Cl. .................................... 128/303 R; 623/6
[58] Field of Search .................... 623/6, 4; 128/303 R

[56] References Cited

U.S. PATENT DOCUMENTS

| 4,136,406 | 1/1979 | Norris | 623/6 |
| 4,190,049 | 2/1980 | Hager et al. | 128/303 R |
| 4,214,585 | 7/1980 | Bailey, Jr. | 128/303 R |
| 4,251,887 | 2/1981 | Anis | 128/303 R X |
| 4,530,117 | 7/1985 | Kelman | 623/6 |
| 4,619,256 | 10/1986 | Horn | 128/303 R |
| 4,643,185 | 2/1987 | Gaba | 128/303 R |

FOREIGN PATENT DOCUMENTS

| 0195881 | 10/1986 | European Pat. Off. | 623/6 |
| 2581535 | 11/1986 | France | 623/6 |

Primary Examiner—Ronald L. Frinks
Attorney, Agent, or Firm—Mason, Fenwick & Lawrence

[57] ABSTRACT

A positioning implement for an intraocular lens comprises an elongated plate-like handle having an upper surface on which a movable pusher having a tapered forward end is mounted for axial reciprocation. A canted finger extends unitarily forwardly from the handle and also has a tapered forward end. Both tapered forward ends are provided with slots dimensioned to fit over an intraocular lens haptic to permit selective application of force to the haptic of an intraocular lens at two different locations for positioning it in the lens capsule of the eye.

16 Claims, 8 Drawing Figures

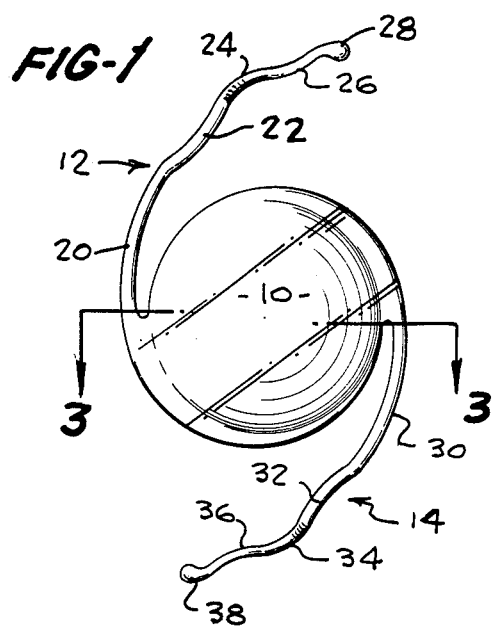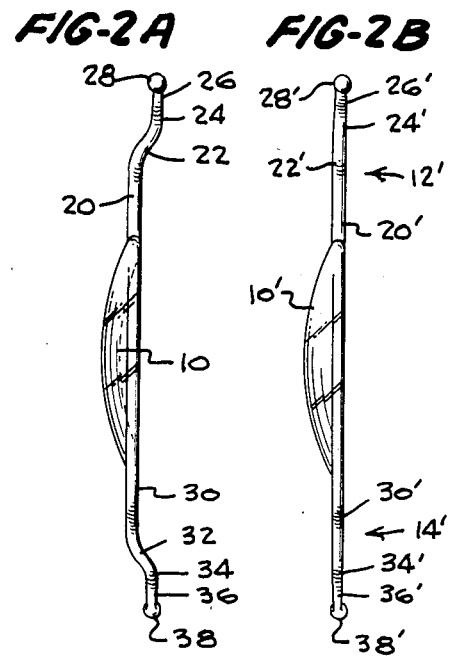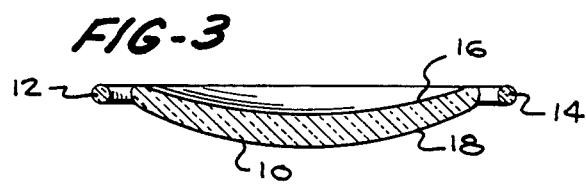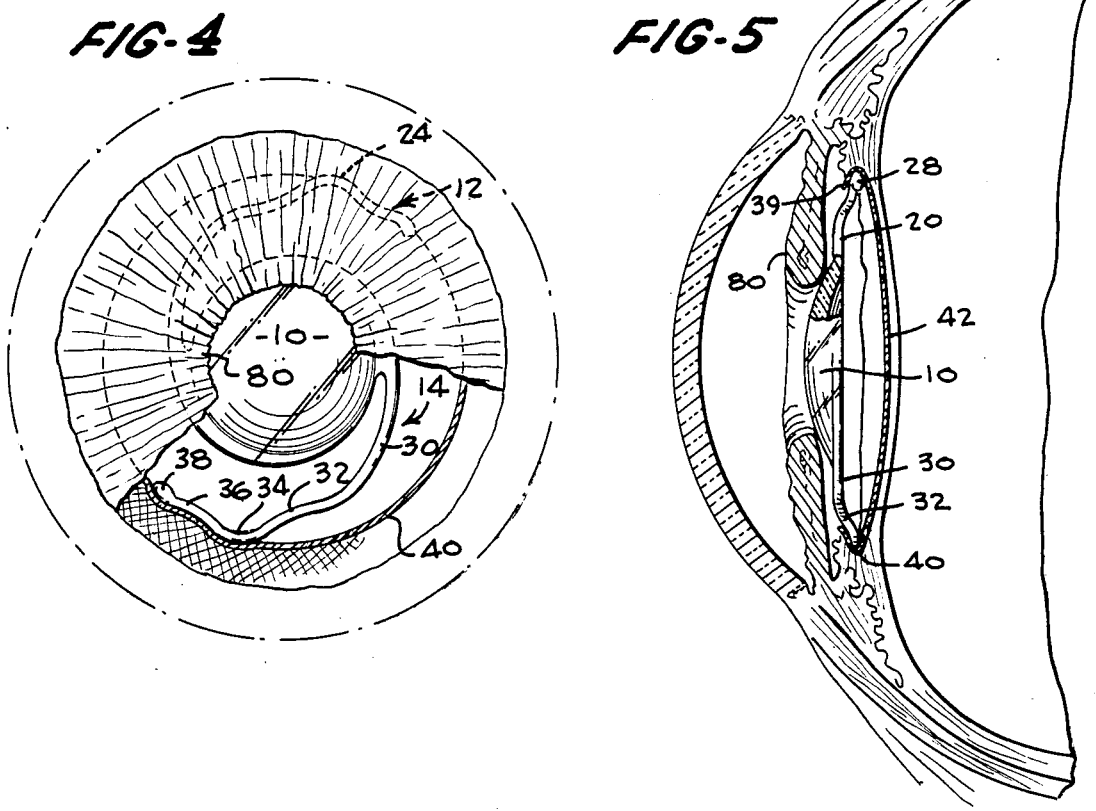

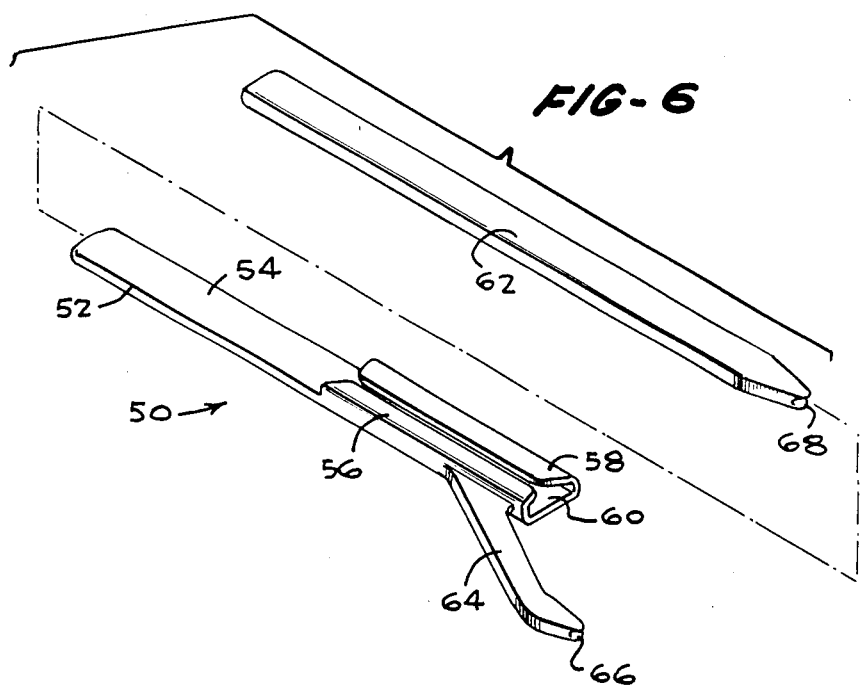
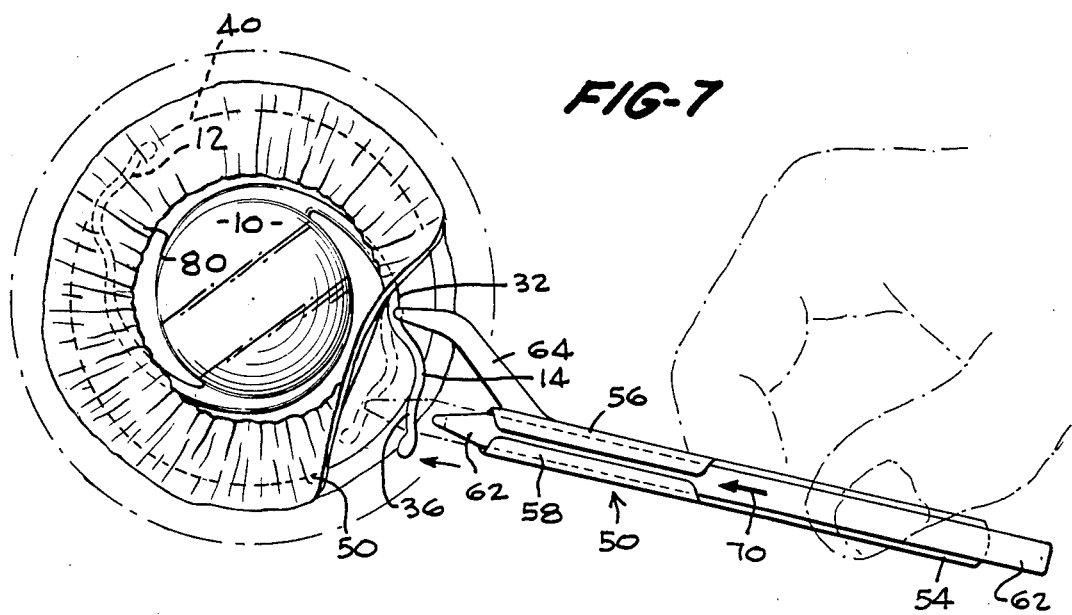

POSITIONING IMPLEMENT FOR INTRAOCULAR LENS

BACKGROUND OF THE INVENTION

The present invention is in the field of intraocular lens devices for correction of aphakia by implantation in the posterior chamber of the human eye. With respect to prior art problems and proposed solutions thereto, reference is made to the description of the development of prior art intraocular lens and various prior patents and publications as discussed and cited in my earlier U.S. Pat. No. 4,328,595.

Notwithstanding the advances in the art represented by the above-noted and other prior art, problems of maintaining flexibility and stability of an intraocular lens in the eye have continued to occur. One particular problem resides in the fact that many of the prior known lenses that curve back upon themselves frequently malfunction as a consequence of the haptic moving out of position whenever the eye is compressed. Another problem resides in the fact that the implantation of an intraocular lens necessarily takes place in a restricted area to which access is difficult. Implantation has been effected by the use of conventional prior known surgical implements and by the use of newly developed special implements designed for implanting a particular type of lens. Unfortunately, many of the tools employed in lens implantation surgery are large in comparison to the size of the lens and are consequently cumbersome and difficult to use. Attempts to solve one or more of the aforementioned problems are demonstrated in U.S. Pat. Nos. 3,436,763; 3,673,616; 3,975,779; 4,080,709; 4,087,866; 4,092,743; 4,104,339; 4,122,556; 4;.136,406; 4,198,714; 4,285,072; 4,370,760; 4,377,873; 4,412,359; 4,451,938; 4,463,457; 4,463,458; 4,490,860; 4,476,591; 4,485,499; 4,490,860; 4,502,162; 4,502,163; 4,503,570; 4,504,981; 4,512,039; 4,512,040 and 4,513,546. Additionally, British Patent No. 2,053,689 also illustrates an attempt to solve one or more of the aforementioned problems.

SUMMARY OF THE INVENTION

It is the primary object of the invention to provide a new and improved implement for positioning an intraocular lens in the lens capsule following removal of the natural lens.

Achievement of the aforementioned and other objects of the invention is enabled by the disclosed implement embodiment which is used with either a vaulted intraocular lens or a non-vaulted intraocular lens. In both lens the lens body is provided with a pair of haptics unitarily formed with the lens body and each comprising four end-to-end connected haptic segments which undulate in alternate manner from the inner connection of the innermost one of set segments to the lens body to an outer bulbous end tip on the outer end of the outermost one of the haptic segments. Stated differently, each haptic segment has a center of curvature with the center curvature of the adjacent haptic segments being on opposite sides of the haptic to provide the undulating shape. The undulating shape of each haptic is of particular value in maintaining the haptic in firm position once it has been implanted. Moreover, the undulating shape is such as to permit usage of a special tool for effecting implantation of the lens in the posterior chamber of the eye with a minimum of difficulty. In one lens embodiment, all of the haptic segments lie in a common plane so as to provide a non-vaulted construction. In the other lens embodiment the haptics include a canted haptic segment between the innermost segment adjacent the lens body and the third outward haptic segment so that the third and fourth haptic segments lie in a plane spaced rearwardly of the plane of the lens body whereas the innermost haptic segment is in alignment with the lens body.

The positioning implement comprises an elongated plate-like handle on which a movable pusher is mounted for axial reciprocation. The handle and the pusher each have tapered forward ends which are offset transversely to each other and each of which has a haptic receiving slot at its forward end spaced apart so as to be engageable with different recesses in a lens haptic. It is consequently possible to apply selective force to the haptic at two spaced locations to aid in positioning it in the capsule.

BRIEF DESCRIPTION OF THE DRAWINGS

FIG. 1 is a front elevation view of the vaulted intraocular lens used with the positioning implement invention;

FIG. 2A is a right side elevation view thereof;

FIG. 2B is a left side elevation view of a second embodiment;

FIG. 3 is a sectional view taken along lines 3—3 of FIG. 1;

FIG. 4 is a front elevation view illustrating the lens of FIG. 1 after positioning in the eye with a portion of the eye being removed for clarity of illustration;

FIG. 5 is a sectional view through the eye illustrating the lens of FIG. 1 following implantation;

FIG. 6 is an exploded perspective view of the preferred embodiment surgical implement of the present invention; and FIG. 7 is a perspective view illustrating usage of the surgical implement of FIG. 6 during the positioning of an intraocular lens in the eye.

DESCRIPTION OF THE PREFERRED EMBODIMENTS

The preferred embodiment of the invention is used for positioning of an intraocular lens which comprises a convex-concave lens 10 formed of polymethylmethacrylate from which first and second haptic members 12 and 14 extend in a generally tangential manner. Lens 10 has a posterior surface 16 and an anterior face 18 as best shown in FIG. 3. It would also be possible to construct the lens 10 in other configurations such as convex-plano if desired.

The first haptic 12 has an inner slightly curved portion 20 having a center curvature which is on the side of portion 20 facing lens 10. A second curve portion 22 is unitarily joined to the outer end of the inner portion 20 and has its center of curvature spaced outwardly from its side facing away from the lens 10. Similarly, a third curved portion 24 extends outwardly from the outer end of the second curved portion 22 in a unitary manner and has its center of curvature on its side facing lens 10. In like manner, a fourth curved portion 26 is unitarily joined and extends from the outer end of the third curved portion 24 and has its center of curvature spaced outwardly from its side facing away from the lens 10. Lastly, a bulbous end portion 28 is provided on the outer end of the fourth curved portion 26. The second haptic 14 is identical to the first haptic 12 and similarly includes an inner curved portion 30 having its center of curvature facing its side facing the lens 10, a second curved portion 32 having a center of curvature outwardly of its side facing away from lens 10, a third curved portion 34 having a center of curvature facing its side facing the lens body 10 and an outer or fourth curved portion 36 having its center of curvature facing its surface which faces away from lens body 10. Additionally, the second haptic 14 includes an outer bulbous end portion 38.

It should further be observed that the second curved portion 22 is canted posteriorly from its inner end to its outer end as shown in FIG. 2A. Additionally, the fourth curved portion 26 is positioned in a plane perpendicular to the axis of the lens 10 and spaced approximately 0.3 mm posteriorly of the lens 10. The outer or fourth curved portion 26 and the bulbous end portion 28 are also positioned in the same plane as the third curved portion 24. In like manner, the second curved portion 32 of the second haptic is canted rearwardly in the same manner as portion 22 of the first haptic and third curved portion 34, fourth curved portion 36 and bulbous end portion 38 are positioned posteriorly of the lens body in the same plane as portions 24, 26 and 28 of the first haptic.

In the non-vaulted lens of FIG. 2B, all portions of the first haptic 12 and the second haptic 14 lie in a common, plane perpendicular to the axis of lens 10 so as to provide a non-vaulted construction. More specifically, haptic 12' comprises inner portion 20', second curved portion 22', third curved portion 24', fourth curved portion 26' and bulbous end portion 28'. Similarly, the second haptic 14' comprises a first curved portion 30', a second curved portion 32', a third curved portion 34', a fourth curved portion 36' and a bulbous end portion 38'. It should be understood that the first and second haptics 12' and 14' are identical in appearance to the haptics 12 and 14 as viewed from the front as in FIG. 1; consequently, the location of the centers of curvature of portions 20', 22', 24' and 26' relative to the haptic are the same as those for portions 20, 22, 24 and 26 of first haptic 12.

Preparation of the eye for receiving either of the above-discussed lens is effected by the conventional extracapsular cataract removal procedure in which the central portion of the anterior wall 39 of the lens capsule is removed so as to leave the equatorial region 40 and the posterior wall 42 of the lens capsule in position as shown in FIG. 5.

The manner in which the positioning of the lens in the eye is effected will now be discussed with initial reference being made to FIGS. 6 and 7. More specifically, a hand held implement 50 is employed for accurately and easily manipulating the lens into permanent position in the eye. Implement 50 is formed of rigid metal or plastic and comprises a handle portion 52 having an upper surface 54 and first and second generally L-shaped guide plates 56 and 58 provided at one end for defining an opening 60 in which an elongated movable pusher 62 is positioned for axial reciprocation on surface 54. Pusher 62 and handle 52 are of rectangular transverse cross-section with pusher 62 being of less width than handle 52 as shown in FIG. 7. Additionally, a finger 63 is fixedly connected to the side of handle portion 52 and includes a rearward portion 64 which extends forwardly and laterally thereof as shown in FIG. 6 and a tapered distal portion oriented with its axis in a plane parallel to the axis of handle 52. The forward end of pusher finger 64 is provided with a U-shaped generally arcuate slot 66 dimensioned so as to be fittable over either of the haptics of the lens assembly. Similarly, the movable pusher 62 is provided with an identical transverse U-shaped or arcuate slot 68 on its forward end so as to be fittable over one of the haptics.

The manner in which the lens is positioned in the eye will now be discussed with reference being made to FIG. 7 in which the eye is illustrated with a previously effected incision used for removal of the natural lens by conventional procedures. The incision provided in the cornea 50 is of adequate size to permit the passage of the haptic 12 to pass through the incision and through the iris 80 so that it is positioned in the equatorial region 40 of the lens capsule as shown in FIG. 7. The positioning of the first haptic 12 is rather easily effected by the use of tweezers or similar surgical implements capable of manipulating the lens assembly. The hand held implement 50 is then used for positioning the second haptic 14 in the lens capsule with such positioning being generally accomplished in two steps. Firstly, implement 50 is grasped in the hand of a user with the movable pusher 62 being in a retracted position as shown in FIG. 7. The slot on the forward end of pusher finger 64 is engaged with the second curved portion 32 of haptic 14 and the implement is moved to the left to position the haptic in the dashed line position of FIG. 7. Movable pusher 62 is then moved forwardly in the direction of arrow 70 so that it engages the haptic in the fourth curved portion 36 and moves it forward to the position shown in dashed lines. Continued movement of the implement to the left permits the haptic 14 to pass through the iris into the posterior chamber of the eye so that it can then be released to move into the equatorial region 40 of the capsular bag. The U-shaped slots on the forward ends of members 62 and 64 permit the haptic to be manipulated forwardly and rearwardly since internal tension in the haptic maintains it in the U-shaped slots during the insertion procedure.

It will also be apparent that only a minimal amount of space is required for use of the implement 50 and that the movable pusher 62 can be easily adjusted to a desired position to give the exact amount of curvature necessary to pass the haptic 14 into the posterior chamber so as to position the lens assembly in the position shown in FIG. 5. Thus, the curved portions 32 and 36 of the haptic cooperate in a unique manner for permitting the positioning of the haptic in the posterior chamber. Also, the portions 34 and 38 in effect constitute foot portions engagable with the equatorial region 40 of the capsule to provide enhanced resistance to rotational movement of the lens. Consequently, the lens is extremely stable after positioning in the eye.

While only a preferred embodiment of the invention has been disclosed, it should be understood that those of skill in the art will undoubtedly conceive of equivalent variations which will not depart from the spirit and scope of the invention which is to be limited solely by the appended claims.

I claim:

1. An implement for effecting the positioning in the posterior chamber of the eye of an intraocular lens of the type comprising a lens body and first and second haptics each having one end extending generally tangentially from the lens body and formed of a plurality of end-to-end sections which alternatingly have respective centers of curvature on opposite sides of the haptic so that the edge of each haptic comprises alternating protrusions and depressions, said implement comprising:
- an elongated handle having a forward end and a pusher finger extending laterally and forwardly from said forward end and including a first pusher tip on the forward end of said pusher finger dimensioned and shaped as to be drivingly engageable with one of said haptics;
- an elongated movable pusher mounted for axial reciprocation on said elongated handle portion and a second pusher tip on a forward-end of said movable pusher; and
- wherein said first pusher tip and said second pusher tip are laterally spaced apart a distance approximately equal the distance between two of said protrusions on one of said haptics.

2. The implement of claim 1 wherein said first and second pusher tips each include an inwardly extending haptic retaining slot on their distal ends dimensioned to each respectively fit over one edge of one of said haptics to retain lateral movement of the haptic relative to the respective pusher tip.

3. The implement of claim 2 additionally including guide means on one end of said handle for preventing lateral movement of said elongated movable pusher relative to said handle.

4. The implement of claim 3 wherein said guide means comprises first and second generally L-shaped guide plates.

5. The implement of claim 4 wherein said pusher finger includes a rearward finger portion oriented at an arcuate angle relative to the axis of said handle and a distal finger portion oriented in a plane parallel to the axis of said handle.

6. The implement of claim 5 wherein said handle and said movable pusher both comprise elongated plate-like members.

7. The implement of claim 6 wherein the distal ends of said handle and said pusher taper inwardly toward their distal ends.

8. The implement of claim 7 wherein said haptic retaining slots are generally arcuate in shape as viewed from one end.

9. The implement of claim 1 wherein said handle and said pusher are of generally rectangular transverse cross-section.

10. The implement of claim 9 wherein said first and second pusher tips each include an inwardly extending haptic retaining slot on their distal ends dimensioned to each respectively fit over one edge of one of said haptics to retain lateral movement of the haptic relative to the respective pusher tip.

11. The implement of claim 10 additionally including guide means on one end of said handle for preventing lateral movement of said elongated movable pusher relative to said handle.

12. The implement of claim 11 wherein said guide means comprises first and second generally L-shaped guide plates.

13. The implement of claim 12 wherein said pusher finger includes a rearward finger portion oriented at an acute angle relative to the axis of said handle and a distal finger portion oriented in a plane parallel to the axis of said handle.

14. The implement of claim 13 wherein said handle and said movable pusher both comprise elongated plate-like members.

15. The implement of claim 14 wherein the distal ends of said handle and said pusher taper inwardly toward their distal ends.

16. The implement of claim 15 wherein said haptic retaining slots are generally arcuate in shape as viewed from one end.

* * * * *